US007707010B2

(12) United States Patent
Wakamiya et al.

(10) Patent No.: US 7,707,010 B2
(45) Date of Patent: Apr. 27, 2010

(54) SAMPLE ANALYZER AND ERROR INFORMATION DISPLAYING METHOD

(75) Inventors: Yuji Wakamiya, Kobe (JP); Tomohiro Okuzaki, Himeji (JP); Hisato Takehara, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/284,146

(22) Filed: Sep. 18, 2008

(65) Prior Publication Data

US 2009/0082984 A1 Mar. 26, 2009

(30) Foreign Application Priority Data

Sep. 20, 2007 (JP) .............................. 2007-243428

(51) Int. Cl.
*G06F 17/40* (2006.01)
(52) U.S. Cl. .................................................... 702/187
(58) Field of Classification Search ................ 702/185, 702/123, 127, 186, 187; 715/705, 708, 709, 715/764, 808

See application file for complete search history.

(56) References Cited

U.S. PATENT DOCUMENTS

| 6,937,964 B2 * | 8/2005 | Okuno et al. ............... 702/187 |
| 7,403,721 B2 * | 7/2008 | Yamada ....................... 399/21 |
| 2005/0036913 A1 * | 2/2005 | Yamakawa et al. ............ 422/65 |

FOREIGN PATENT DOCUMENTS

| JP | 2002-116212 | 4/2002 |
| JP | 2006-071649 | 3/2006 |

* cited by examiner

*Primary Examiner*—Drew A Dunn
*Assistant Examiner*—Stephen J Cherry
(74) *Attorney, Agent, or Firm*—Brinks Hofer Gilson & Lione

(57) ABSTRACT

The invention provides a sample analyzer by which a position of any error status in the sample analyzer can be easily found by a user to allow the user to carry out an error recovery operation in an accurate and prompt manner. The sample analyzer 1 comprises a sensor for detecting a status of a measurement unit 2 including an error status; a display section 400b; and a controller 400a for controlling the display section 400b so as to display recovery information for recovering the measurement unit 2 from the error status and an error-occurring place image regarding a place where an error has occurred, when the sensor detects the error status of the measurement unit 2.

13 Claims, 11 Drawing Sheets

FIG. 11

| No. | Text display | Display color | Error recovery icon | Status |
|---|---|---|---|---|
| 1 | Measurement impossible | Gray | No | Apparatus power source OFF status or the like |
| 2 | Pause | Blue | No | Pause mode (e.g., sleep status) |
| 3 | Reagent storage | | No | Cooling status of reagent or the like |
| 4 | Standby | Green | No | Measurement can be started immediately. |
| 5 | Startup | | No | Stable temperature is waited after turning ON of power source. |
| 6 | Error | | No | Error measurement can be started. |
| 7 | Startup | | No | Under initial operation |
| 8 | Under measurement | | No | Under measurement operation |
| 9 | Measurement reservation | | No | Measurement is started after preparation for measurement is completed. |
| 10 | Under operation | | No | Maintenance operation is being carried out. |
| 11 | Being interrupted | Yellow |  | Interruption button is operated. Measurement can be started. |
| 12 | Error | |  | New sucking is stopped. Measurement can be started directly. |
| 13 | Error | |  | Measurement can be started after reset of rack. |
| 14 | Error | |  | Measurement cannot be started until measurement is completed. |
| 15 | Error | Red | No | Fatal error occurs. |

SAMPLE ANALYZER AND ERROR INFORMATION DISPLAYING METHOD

RELATED APPLICATIONS

This application claims priority under 35 U.S.C. §119 to Japanese Patent Application No. JP2007-243428 filed Sep. 20, 2007, the entire content of which is hereby incorporated by reference.

BACKGROUND OF THE INVENTION

1. Field of the Invention

The present invention relates to a sample analyzer for analyzing sample such as an immunity analyzer and a blood coagulation analyzer, and a method for displaying error information of the sample analyzer.

2. Description of the Related Art

In hospitals and inspection agencies, sample analyzers have been used to measure properties of a sample (e.g., blood) collected from a living organism. Japanese Unexamined Patent Publication No. 2006-71649 discloses a living body sample analyzer designed to display, when an error such as a malfunction occurs, the explanation of the error or a method for recovering the error on a display screen of a control apparatus. This apparatus allows a user to read the explanation displayed on the display screen for example to recognize the details of the error to carry out a recovery operation.

In the case of the technique of the above publication, the explanation of the error and the method for recovering the error are merely displayed on the display screen. Thus, the amount of information for the method for recovering the error is limited. This has caused a case where general users having such a limited amount of information are prevented from carrying out the recovery operation. In such a case, the users were forced to refer to a manual to find the description for the error or to call a service center to ask for a recovery method. This has caused a risk where the error recovery operation requires a long time to hinder an inspection activity.

SUMMARY OF THE INVENTION

The present invention has been made in view of the situation as described above. It is an objective of the present invention to provide a sample analyzer by which a position of any error status in the sample analyzer can be easily found by a user to allow the user to carry out an error recovery operation in an accurate and prompt manner, and a method for displaying error information of the sample analyzer.

In accordance with a first aspect of the present invention, there is provided a sample analyzer comprising: a detector for detecting status of the sample analyzer including error status; a display; and a display controller for controlling the display so as to display recovery information for recovering the sample analyzer from the error status and an error-occurring place image regarding a place where an error has occurred, when the detector detects the error status.

In accordance with a second aspect of the present invention, there is provided a sample analyzer comprising: a detector for detecting status of the sample analyzer including error status; a display; and a display controller for controlling the display so as to display an icon image showing a recovery procedure for recovering the sample analyzer from the error status, when the detector detects the error status.

In accordance with a third aspect of the present invention, there is provided a method for displaying error information of a sample analyzer for analyzing a sample, comprising steps of: (a) detecting status of the sample analyzer including error status; and (b) displaying, on the display, recovery information for recovering the sample analyzer from the error status and an error-occurring place image regarding a place where an error has occurred, when the error status is detected in the step (a).

In accordance with a fourth aspect of the present invention, there is provided a method for displaying error information of a sample analyzer for analyzing a sample, comprising steps of: (a) detecting status of the sample analyzer including error status; and (b) displaying, on a display, an icon image showing a recovery procedure for recovering the sample analyzer from the error status, when the error status is detected in the step (a).

BRIEF DESCRIPTION OF THE DRAWINGS

FIG. 11 is a table showing the correspondence among text displays, display colors, error recovery icons, and apparatus statuses of the apparatus status display area.

DETAILED DESCRIPTION OF THE INVENTION

Hereinafter, an embodiment of a sample analyzer of the present invention will be described in detail with reference to the attached drawings.

[Entire Configuration of the Apparatus]

Figure 1:
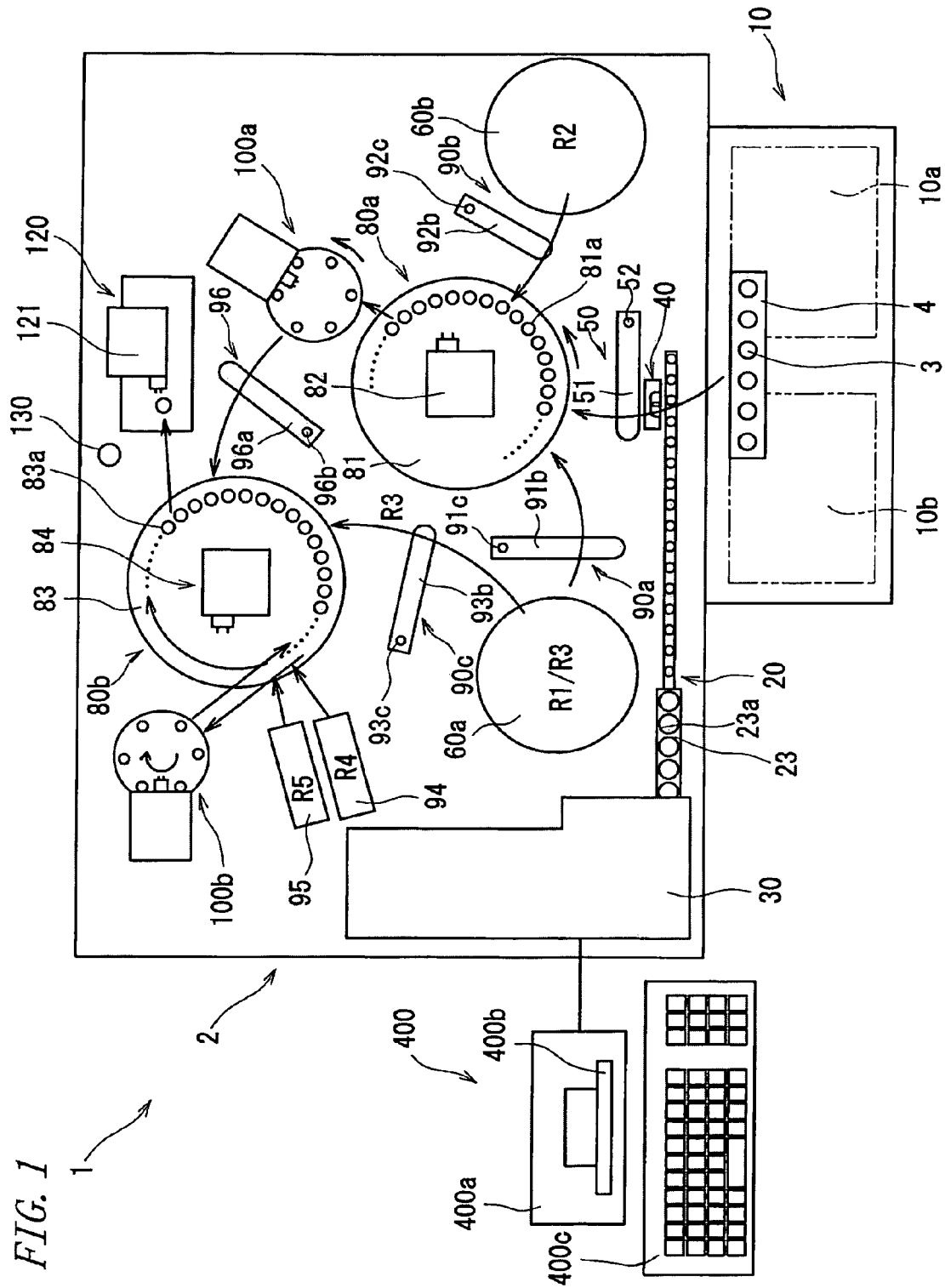
FIG. 1 is a top view illustrating the entire configuration of one embodiment of a sample analyzer of the present invention.

An immunity analyzer 1 according to one embodiment of the present invention is an apparatus for using a sample such as blood to carry out the inspection of various items such as a type B hepatitis, a type C hepatitis, a tumor marker, and a thyroid hormone. This immunity analyzer 1 is mainly composed, as schematically shown in FIG. 1, of a measurement unit (measurement section) 2 consisting of a plurality of mechanisms (components); and a control apparatus 400 (see FIG. 3) that is a data processing unit electrically connected to this measurement unit 2.

Figure 2:
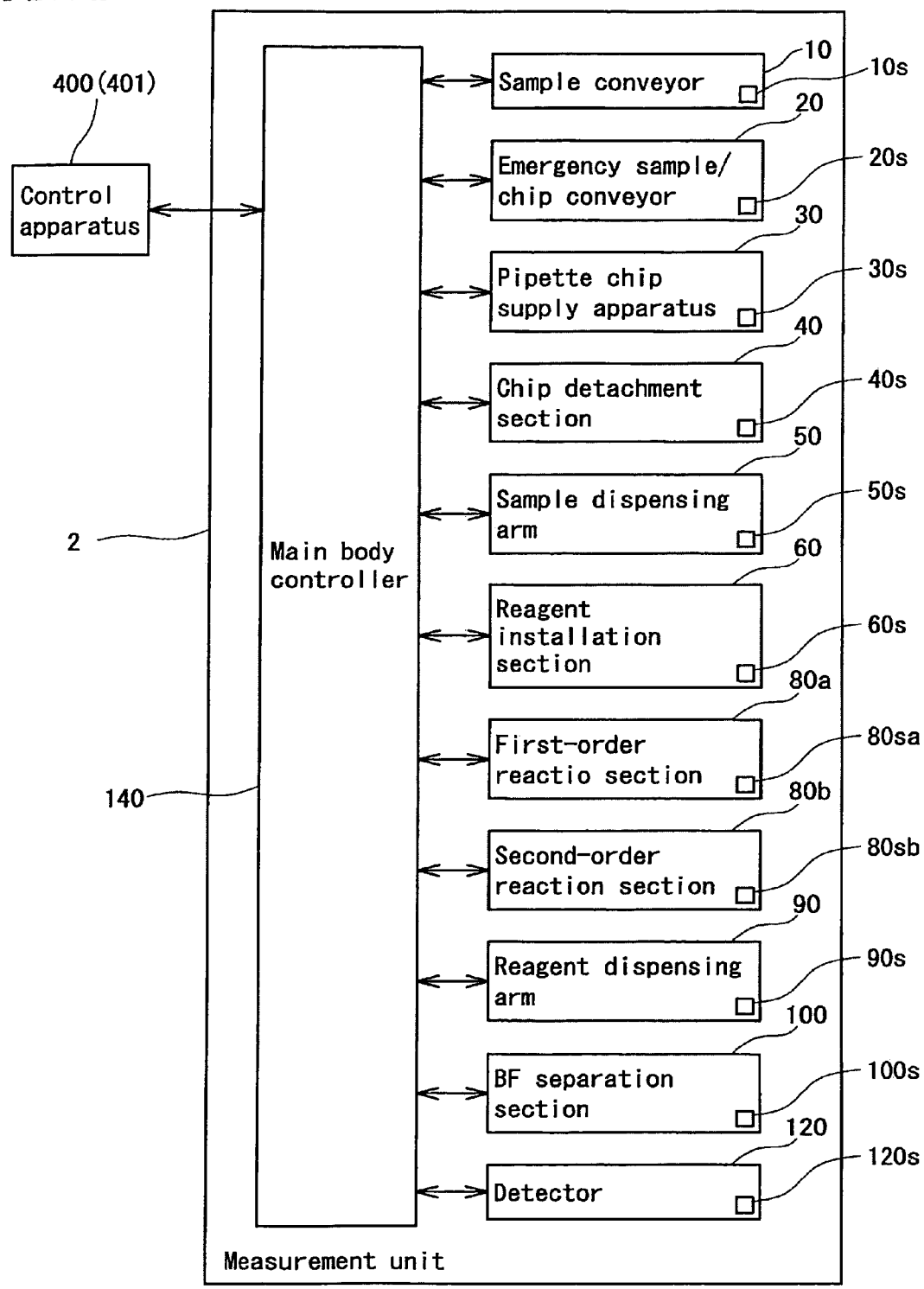
FIG. 2 is a block diagram illustrating the configuration of a measurement unit in an immunity analyzer shown in FIG. 1.

The measurement unit 2 includes: a sample conveyor (sampler) 10; an emergency sample/chip conveyor 20; a pipette chip supply apparatus 30; a chip detachment section 40; a sample dispensing arm 50; a reagent installation sections 60a and 60b; a first-order reaction section 80a and a second-order reaction section 80b; reagent dispensing arms 90a, 90b, and 90c; a first BF separation section 100a and a second BF separation section 100b; a detector 120; and a main body controller 140 (see FIG. 2) for controlling the operations of mechanisms such as the sample conveyor (sampler) 10 and the sample dispensing arm 50. It is noted that, in the immunity analyzer 1 according to this embodiment, a disposable pipette chip is exchanged with the new one whenever a sample is sucked and discharged in order to restrain a sample (e.g., blood) sucked and discharged by the sample dispensing arm 50 from being mixed with other samples.

In this immunity analyzer 1, a capture antibody (reagent R1) bound to an antigen included in a sample (e.g., blood) as a measurement target is allowed to be bound to magnetic particles (reagent R2) to prepare a complex of antigen-capture antibody-magnet particles. Thereafter, the complex of antigen-capture antibody-magnetic particles is attracted by a magnet of a first Bound Free (BF) separation section 100a, thereby removing the reagent R1 including unreacted (free) capture antibody. Then, the antigen of the complex is bound to a labeled antibody (reagent R3) to prepare a complex of antigen-capture antibody-magnetic particles-labeled antibody. Thereafter, the complex of antigen-capture antibody-magnetic particles-labeled antibody is attracted by a magnet of a second BF separation section 100b, thereby removing the reagent R3 including an unreacted (free) labeled antibody. Thereafter, a luminescent substrate (reagent R5) that emits light in a process of the reaction with the labeled antibody is added to subsequently measure the light emission amount caused by the reaction between the labeled antibody and the luminescent substrate. Through the process as described above, the antigen included in the sample bound to the labeled antibody is measured quantitatively.

[Configuration of Control Apparatus]

The control apparatus 400 is composed of a personal computer 401 (PC) for example. As shown in FIG. 1, the control apparatus 400 includes: a controller 400a; a display section 400b; and an input section (input means) 400c such as a keyboard or a mouse. The controller 400a has a function to control the operations of the respective mechanisms in the measurement unit 2 and to analyze the optical information for the sample obtained by the measurement unit 2. This controller 400a is composed of CPU, ROM, and RAM for example. The display section 400b is used to display the information for the analysis result obtained by the controller 400a or to display an error window (measurement section help window) 210 (which will be described later) or the like.

Figure 3:
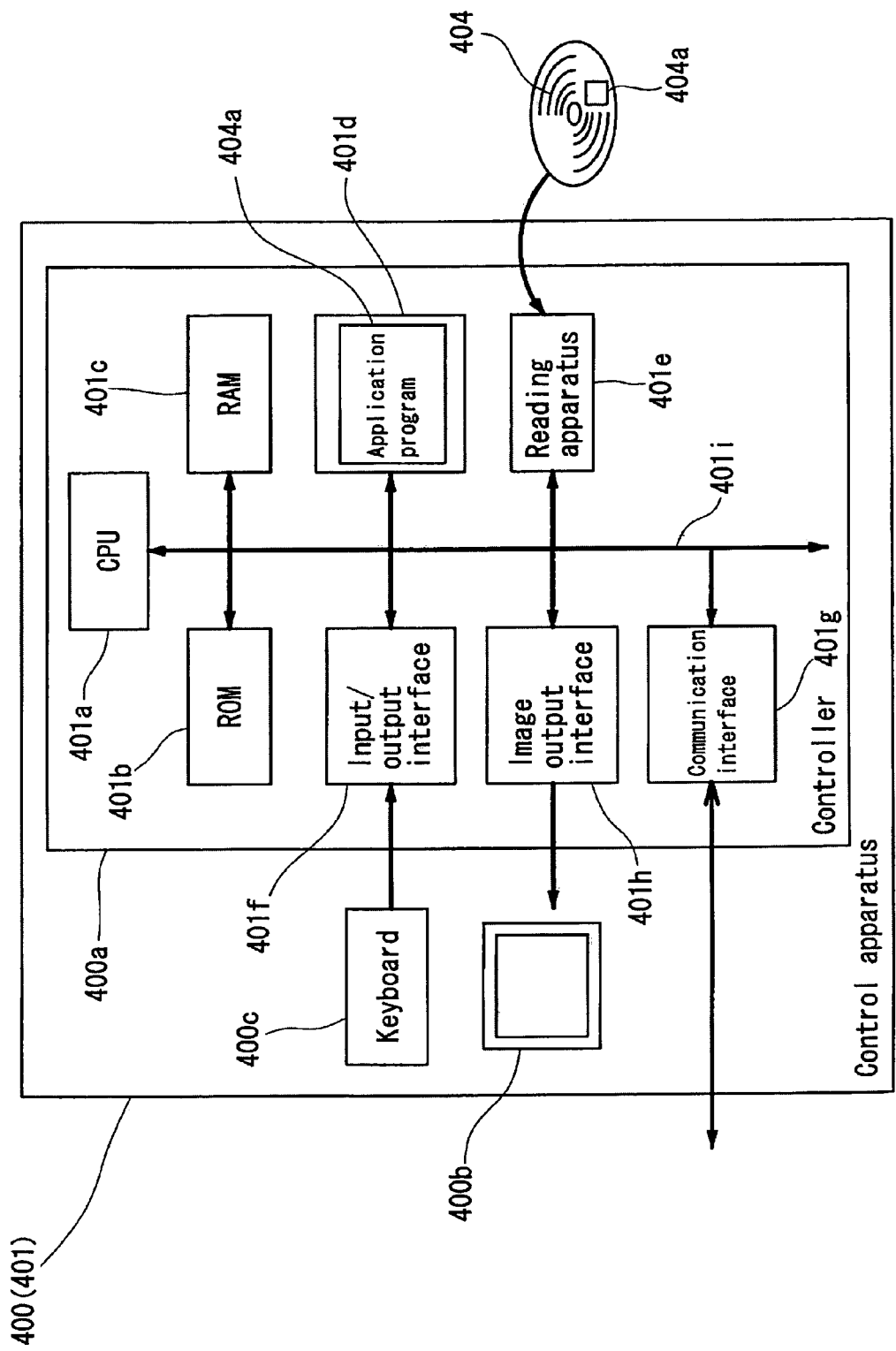
FIG. 3 is a block diagram illustrating a control apparatus in the immunity analyzer shown in FIG. 1.

Next, the configuration of the control apparatus 400 will be described. As shown in FIG. 3, the controller 400a is mainly composed of: a CPU 401a; a memorization section consisting of a ROM 401b, a RAM 401c, and a hard disk 401d or the like; a reading apparatus 401e; an input/output interface 401f; a communication interface 401g; and an image output interface 401h. The CPU 401a, the ROM 401b, the RAM 401c, the hard disk 401d, the reading apparatus 401e, the input/output interface 401f, the communication interface 401g, and the image output interface 401h are connected by a bus 401i.

The CPU 401a can execute a computer program memorized in the ROM 401b and a computer program loaded to the RAM 401c. By allowing the CPU 401a to execute an application program 404a (which will be described later), the computer 401 functions as the control apparatus 400. The ROM 401b is composed of a mask ROM, PROM, EPROM, EEPROM or the like in which the computer program executed by the CPU 401a and the data used for this or the like are recorded.

The RAM 401c is composed of a SRAM or DRAM or the like. The RAM 401c is used to read a computer program recorded in the ROM 401b and the hard disk 401d. The RAM 401c is also used as an operation region of the CPU 401a when these computer programs are executed.

In the hard disk 401d, various computer programs 404a such as an operating system and an application program to be executed by the CPU 401a and data used to execute the computer programs are installed. For example, an application program for registering a measurement order and an application program for acquiring or displaying the information for an error of the measurement unit 2 as will be described later are also installed in this hard disk 401d. The hard disk 401d memorizes an abnormal place image, an error details message, a background image of the apparatus status display area 202, and an error recovery icon that are associated with apparatus status and that will be described later.

The reading apparatus 401e is composed of a flexible disk drive, a CD-ROM drive, a DVD-ROM drive or the like. The reading apparatus 401e can read a computer program or data recorded in a mobile recording medium 404. The mobile recording medium 404 stores therein the application program 404a in this embodiment. The computer 401 can read the application program 404a from the mobile recording medium 404 to install the application program 404a in the hard disk 401d.

It is noted that the application program 404a can be provided not only from the mobile recording medium 404 but also from an external device connected to the computer 401 to have communication therebetween via an electric communication line (which may be wired or wireless). For example, the application program 404a also can be stored in a hard disk of a server computer on the Internet and the computer 401 may access this server computer to download the application program 404a to install the application program 404a in the hard disk 401d.

In the hard disk 401d, an operating system providing a graphical user interface environment such as Windows® manufactured and sold by Microsoft Corporation is installed for example. The following description assumes that the application program 404a in this embodiment operates on the operating system.

The input/output interface 401f is composed, for example, of a serial interface such as a USB, IEEE1394 or RS-232C, a parallel interface such as an SCSI, IDE or IEEE1284, and an analog interface comprising a D/A converter, an A/D converter or the like. The input/output interface 401f is connected to the keyboard 400c. A user can use the keyboard 400c to input data to the computer 401.

The communication interface 401g is an Ethernet® interface for example. The computer 401 can use the communication interface 401g to use a predetermined communication protocol to send data to and to receive data from the measurement unit 2. The image output interface 401h is connected to the display section 400b composed of a LCD, a CRT or the like. The image output interface 401h is structured to output, to the display section 400b, a video signal depending on image data given from the CPU 401a. Based on the inputted video signal, the display section 400b displays an image (screen).

[Configurations of the Respective Mechanisms of Immunity Analyzer]

The respective mechanisms of the immunity analyzer 1 may use a known configuration. The following section will describe the configurations of the respective mechanisms of the immunity analyzer 1.

A sample conveyor 10 is configured to transport a rack 4 holding a plurality of test tubes 3 accommodating samples to a position corresponding to the sucking position of the sample dispensing arm 50. This sample conveyor 10 has: a rack setting section 10*a* for setting the rack 4 holding the test tubes 3 accommodating unprocessed samples; and a rack reservoir 10*b* for reserving the rack 4 holding the test tube 3 accommodating samples already subjected to the dispensing processing. The sample conveyor 10 transports the test tube 3 accommodating unprocessed samples to the position corresponding to the sucking position of the sample dispensing arm 50. As a result, the samples (e.g., blood) in the test tube 3 are sucked by the sample dispensing arm 50 and the rack 4 holding the test tube 3 is reserved by the rack reservoir 10*b*.

An emergency sample/chip conveyor 20 is configured to transport, to the attachment position of the sample dispensing arm 50, the test tube 3 accommodating an emergency sample that must be inspected prior to samples transported by the sample conveyor 10.

A pipette chip supply apparatus 30 has a function to place inputted pipette chips one by one in a chip installation section 23*a* of a transport rack 23 of the emergency sample/chip conveyor 20.

A chip detachment section 40 is provided to disengage a pipette chip attached to the sample dispensing arm 50 (which will be described later).

The sample dispensing arm 50 has a function to dispense the samples in the test tube 3 transported by the sample conveyor 10 to the sucking position into cuvettes (not shown) retained in a retaining section 81*a* of a rotary table section 81 of a first-order reaction section 80*a* which will be described later. This sample dispensing arm 50 is configured to rotate an arm section 51 around an axis 52 and to move the arm section 51 in an up-and-down direction (direction Z). At a tip end of the arm section 51, a nozzle section for sucking and discharging samples is provided. A tip end of this nozzle section is attached with a pipette chip transported by a transport rack (not shown) of the emergency sample/chip conveyor 20.

A reagent installation section 60*a* includes a reagent container accommodating the reagent R1 including a capture antibody and a reagent container accommodating the reagent R3 including a labeled antibody. On the other hand, a reagent installation section 60*b* includes a reagent container accommodating the reagent R2 including magnetic particles.

The first-order reaction section 80*a* is provided to transfer the cuvette retained by the retaining section 81*a* of the rotary table section 81 while rotating the cuvette by a predetermined angle whenever a predetermined period (20 seconds in this embodiment) is reached to agitate the sample, the reagent R1 and the reagent R2 in the cuvette. Specifically, the first-order reaction section 80*a* is provided to cause, in the cuvette, the reagent R1 having capture antibody to react with the antigen in the sample, and the reagent R1 having capture antibody to react with the reagent R2 having magnetic particles. This first-order reaction section 80*a* is composed of: the rotary table section 81 for transporting the cuvette accommodating the sample, the reagent R1, and the reagent R2 in the rotating direction; and a container conveyor 82 for agitating the sample, the reagent R1, and the reagent R2 in the cuvette 8 and transporting the cuvette 8 accommodating the agitated sample, the reagent R1, and the reagent R2 to a first BF separation section 100*a* (which will be described later).

The container conveyor 82 is provided at the center of the rotary table section 81 in a rotatable manner. This container conveyor 82 has a function to grasp the cuvette retained by the retaining section 81*a* of the rotary table section 81 and to agitate the sample in the cuvette. The container conveyor 82 also has a function to transport, to the first BF separation section 100*a*, a cuvette accommodating a sample obtained by agitating the sample, the reagent R1, and the reagent R2 to incubate the mixture.

A reagent dispensing arm 90*a* has a function to suck the reagent R1 in a reagent container provided in the reagent installation section 60*a* to dispense the sucked reagent R1 into the cuvette of the first-order reaction section 80*a*. This reagent dispensing arm 90*a* is configured to rotate an arm section 91*b* around an axis 91*c* and to move the arm section 91*b* in the up-and-down direction. A tip end of the arm section 91*b* is attached with a nozzle for sucking and discharging the reagent R1 in the reagent container.

A reagent dispensing arm 90*b* has a function to dispense the reagent R2 in the reagent container provided in the reagent installation section 60*b* into the cuvette of the first-order reaction section 80*a* in which the sample and the reagent R1 are dispensed. This reagent dispensing arm 90*b* is configured so that an arm section 92*b* can be rotated around an axis 92*c* and can be moved in the up-and-down direction (direction Z). A tip end of the arm section 92*b* is attached with a nozzle for sucking and discharging the reagent R2 in the reagent container.

In this embodiment, the first BF separation section 100*a* is provided to isolate the unreacted reagent R1 (unnecessary component) and magnetic particles from the sample in the cuvette transported by the container conveyor 82 of the first-order reaction section 80*a*.

The cuvette of the first BF separation section 100*a* accommodating the isolated unreacted reagent R1 or the like is transported by a transport mechanism 96 to a retaining section 83*a* of a rotary table section 83 of a second-order reaction section 80*b*. The transport mechanism 96 is configured to rotate an arm section 96*a* having a cuvette grasp section (not shown) at a tip end around an axis 96*b* and to move the arm section 96*a* in the up-and-down direction (direction Z).

The second-order reaction section 80*b* has the same configuration as that of the first-order reaction section 80*a*. The second-order reaction section 80*b* is provided to rotate the cuvette retained by the retaining section 83*a* of the rotary table section 83 by a predetermined angle whenever a predetermined period (20 seconds in this embodiment) is reached to transfer the cuvette and to agitate the complex of antigen-capture antibody-magnetic particles, the reagent R3, and the reagent R5 in cuvette. Specifically, the second-order reaction section 80*b* is provided to cause, in the cuvette, the reagent R3 having the labeled antibody to react with the antigen in the sample and to cause the reagent R5 having the luminescent substrate to react with the labeled antibody of the reagent R3. This second-order reaction section 80*b* is composed of: the rotary table section 83 for transporting the cuvette 8 accommodating the sample, the reagent R1, the reagent R2, the reagent R3, and the reagent R5 in the rotating direction; and a container conveyor 84 for agitating the sample, the reagent R1, the reagent R2, the reagent R3, and the reagent R5 in the cuvette and transporting the cuvette accommodating the agitated sample or the like to the second BF separation section 100*b* (which will be described later). The container conveyor 84 also has a function to transport the cuvette processed by the second BF separation section 100*b* to the retaining section 83*a* of the rotary table section 83 again.

The reagent dispensing arm 90*c* has a function to suck the reagent R3 in the reagent container provided in the reagent installation section 60*a* to dispense the sucked reagent R3 to the cuvette of the second-order reaction section 80*b* in which the sample, the reagent R1 and the reagent R2 are dispensed. This reagent dispensing arm 90*c* is configured to rotate an arm section 93*b* around an axis 93*c* and move the arm section 93*b* in the up-and-down direction. A tip end of the arm section 93b is attached with a nozzle for sucking and discharging the reagent R3 in the reagent container.

The second BF separation section 100b has the same configuration as that of the first BF separation section 100a. The second BF separation section 100b is provided to isolate the unreacted reagent R3 (unnecessary component) and magnetic particles from the sample in the cuvette transported by the container conveyor 84 of the second-order reaction section 80b.

A reagent R4 supply section 94 and a reagent R5 supply section 95 are provided to supply the reagent R4 and the reagent R5 to the cuvette retained by the retaining section 83a of the rotary table section 83 of the second-order reaction section 80b, respectively.

A detector 120 is provided to obtain, through a photo multiplier tube, the light caused by the reaction process between a labeled antibody bound to the antigen of the sample subjected to a predetermined processing and the luminescent substrate to measure the amount of the antigen included in the sample. This detector 120 includes a transport mechanism section 121 to transport the cuvette retained by the retaining section 83a of the rotary table section 83 of the second-order reaction section 80b to the detector 120.

A used cuvette from which a measured sample is already sucked is disposed, via a disposal hole 130, in a dust box (not shown) provided at the lower part of the immunity analyzer 1.

[Entire Process]

Figure 4:
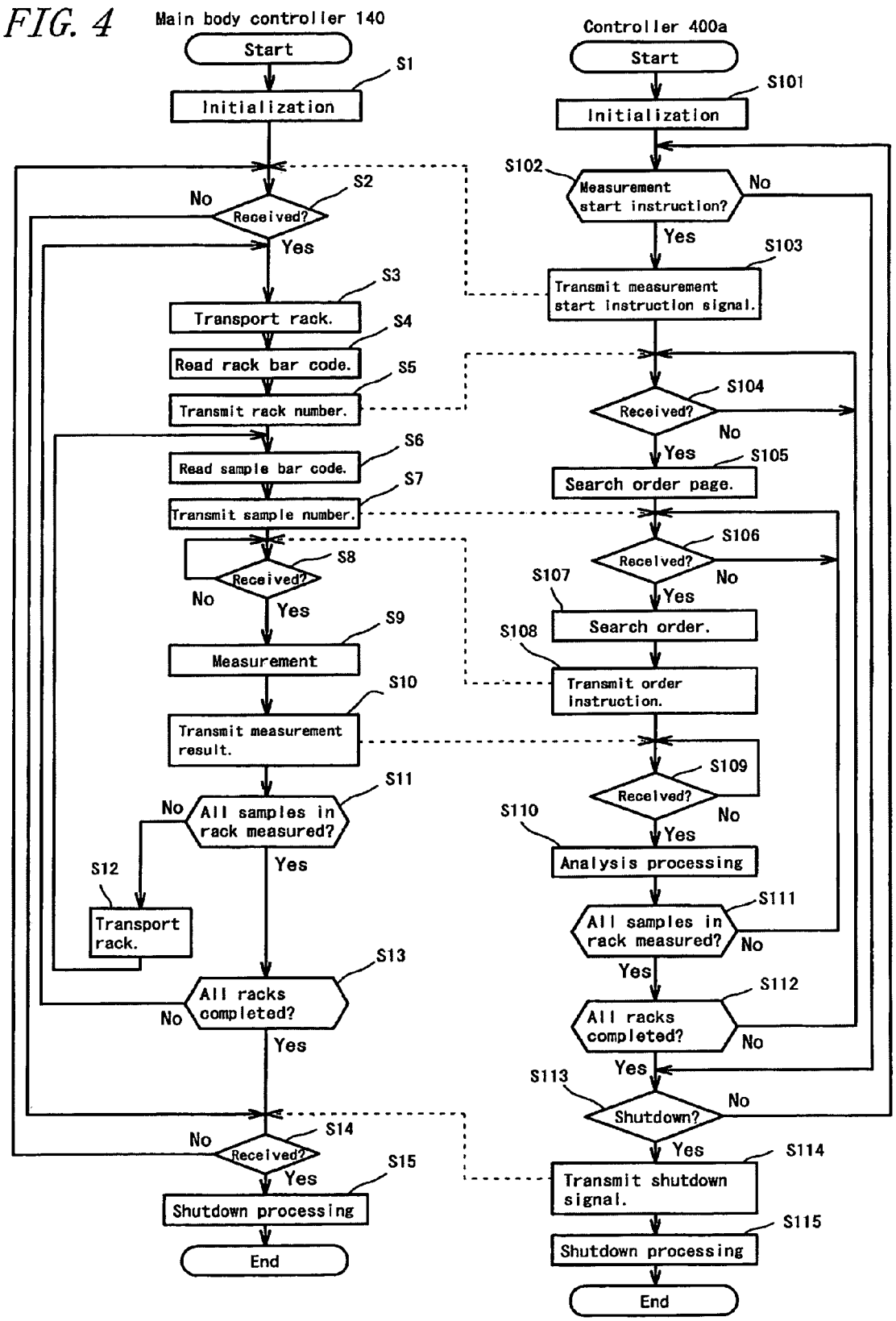
FIG. 4 shows the entire flow of an immunoanalytical process using the immunity analyzer shown in FIG. 1.

The flow of the entirety of the analysis processing by the immunity analyzer 1 is shown in FIG. 4. It is noted that the processing which will be described hereinafter is a processing controlled by the controller 400a and the main body controller 140.

First, when the power source of the immunity analyzer 1 is turned ON, the main body controller 140 is initialized (Step S1). In this initialization operation, the program is initialized and the driving part of the immunity analyzer 1 is returned to the original position for example.

When the power source of a personal computer 401 connected to the immunity analyzer 1 so as to have communication therebetween is turned ON, the controller 400a of the personal computer 401 is initialized (Step S101). This initialization operation initializes a program for example.

Next, the controller 400a in Step S102 determines whether an instruction for the start of the measurement is issued or not. When the controller 400a determines that the instruction for the start of the measurement is issued (Yes), the processing proceeds to Step S103. When the controller 400a determines that the instruction for the start of the measurement is not issued (No), the processing proceeds to Step S113. Then, Step S103 allows a measurement start signal to be sent from the controller 400a to the main body controller 140.

Next, the main body controller 140 in Step 2 determines whether the reception of a measurement start signal is performed or not. When the main body controller 140 determines that the reception of a measurement start signal is performed (Yes), the processing proceeds to Step S3. When the main body controller 140 determines that the reception of a measurement start signal is not performed (No), the processing proceeds to Step S14.

Next, the rack 4 holding a plurality of test tubes 3 accommodating samples is transported by the sample conveyor 10 in Step S3 to a position corresponding to the sucking position 1a of the sample dispensing arm 50. The rack 4 is given with a bar code as a recording section on which information (rack number) for identifying the rack 4 is recorded. The bar code is read by a detector (not shown) provided in a transport path through which the rack 4 is transported to a predetermined position (Step S4). The read rack number is transmitted by the main body controller 140 in Step S5 to the personal computer 401.

Next, the controller 400a in Step S104 determines whether the reception of the rack number is performed or not. When the controller 400a determines that the reception of the rack number is performed (Yes), the processing proceeds to Step S105.

Next, Step S105 allows the controller 400a to search an order page. Specifically, the controller 400a searches the order information corresponding to the rack number received in Step S104 from among the order information memorized in the memorization region of the hard disk 401d.

As in the rack 4, the test tube 3 is given with a bar code that is a recording section on which the information (sample number) for identifying the sample in the test tube 3 is recorded. The bar code is read by a detector (not shown) provided in a transport path through which the rack 4 holding the test tube 3 is transported to a predetermined position (Step S6). The read sample number is sent in Step S7 to the personal computer 401. It is noted that the bar code of the test tube 3 and the bar code of the rack 4 may be read by different detectors or may be read by a common detector.

Next, Step S106 allows the controller 400a to determine whether the reception of the sample number is performed or not. When the controller 400a determines that the reception of the sample number is performed (Yes), the processing proceeds to Step S107.

Next, Step S107 allows the controller 400a to search the order. Specifically, the controller 400a searches the order information corresponding to the sample number received in Step S106 from among the order information corresponding to the specific rack number searched in Step S105. Then, Step S108 allows the controller 400a to send the order instruction to the main body controller 140.

Next, Step S8 allows the main body controller 140 to determine whether the reception of the order instruction is performed or not. When the main body controller 140 determines that the reception of the order instruction is performed (Yes), the processing proceeds to Step S9.

Next, Step S9 carries out the measurement of the ordered item. Then, the measurement result is sent by the main body controller 140 to the personal computer 401 (Step S110).

Next, Step S109 allows the controller 400a to determine whether the reception of the measurement result is performed or not. When the controller 400a determines that the reception of the measurement result is performed (Yes), the processing proceeds to Step S110.

Step S110 subjects the measurement result sent from the main body controller 140 to an analysis processing. Specifically, based on the transmitted measurement result and a calibration curve that is prepared by a standard sample in advance and that is memorized in the hard disk 401d, the controller 400a calculates the concentration of the antigen of the measurement target to memorize the result (analysis result). The controller 400a outputs the analysis result.

Next, Step S111 allows the controller 400a to determine whether the samples in the test tubes 3 held by the rack 4 are all measured or not. When the controller 400a determines that the samples in the test tubes 3 held by the rack 4 are all measured (Yes), the processing proceeds to Step S112. When the controller 400a determines that not all of the samples in the test tubes 3 held by the rack 4 are measured (No), the processing returns to Step S106.

Next, Step S112 allows the controller 400a to determine whether all of the racks 4 are measured or not. When the controller 400a determines that all of the racks 4 are measured (Yes), the processing proceeds to Step S113. When the controller 400a determines that not all of the racks 4 are measured (No), the processing returns to Step S104.

Next, Step S113 allows the controller 400a to determine whether an instruction to shut down the personal computer 401 is accepted or not. When the controller 400a determines that an instruction to shut down the personal computer 401 is accepted (Yes), the processing proceeds to Step S114. When the controller 400a determines that an instruction to shut down the personal computer 401 is not accepted (No), the processing returns to Step S102.

Next, Step S114 allows the shutdown signal to be sent from the controller 400a to the main body controller 140.

Then, Step S115 allows the controller 400a to shut down the personal computer 401, thereby completing the processing.

Step S11 allows the main body controller 140 to determine whether the samples in the test tubes 3 held by the rack 4 are all measured or not. When the main body controller 140 determines that the samples in the test tubes 3 held by the rack 4 are all measured (Yes), the processing proceeds to Step S13. When the main body controller 140 determines that not all of the samples in the test tubes 3 held by the rack 4 are measured (No), the rack 4 is transported by a predetermined distance (a distance along which a test tube accommodating a sample to be measured next reaches a to-be-sucked position) (Step S12). Then, the processing returns to Step S6.

Next, Step S13 allows the main body controller 140 to determine whether all of the racks 4 are measured or not. When the main body controller 140 determines that all of the racks 4 are measured (Yes), the processing proceeds to Step S14. When the main body controller 140 determines that not all of the racks 4 are measured (No), the processing returns to Step S3.

Next, Step S14 allows the main body controller 140 to determine whether the reception of the shutdown signal is performed or not. When the main body controller 140 determines that the reception of the shutdown signal is performed (Yes), the processing proceeds to Step S15. When the main body controller 140 determines that the reception of the shutdown signal is not performed (No), the processing returns to Step S2.

Then, Step S15 allows the main body controller 140 to shut down the immunity analyzer 1, thereby completing the processing.

[Operation Status Check Processing]

Next, an operation status check processing will be described.

Figure 5:
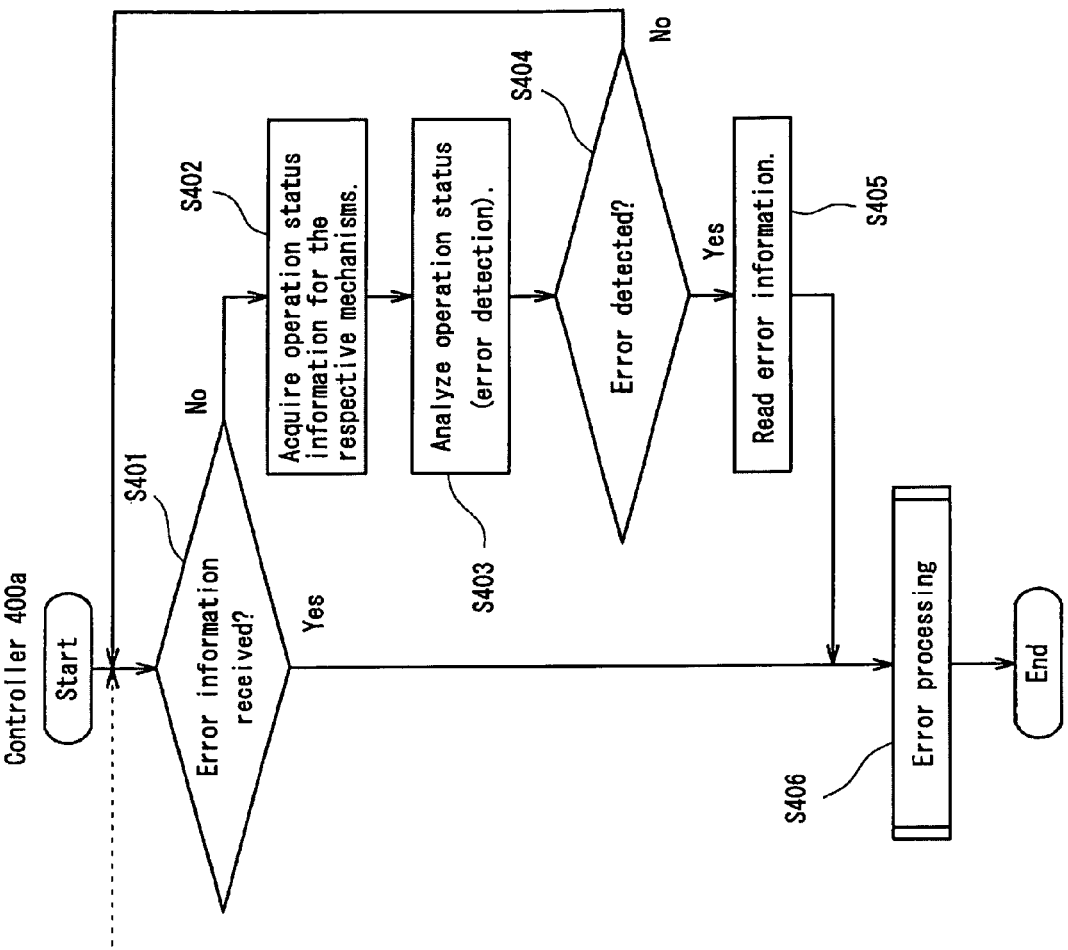
FIG. 5 is a flowchart illustrating the procedure of the operation status check processing of the immunity analyzer.
Figure 5:
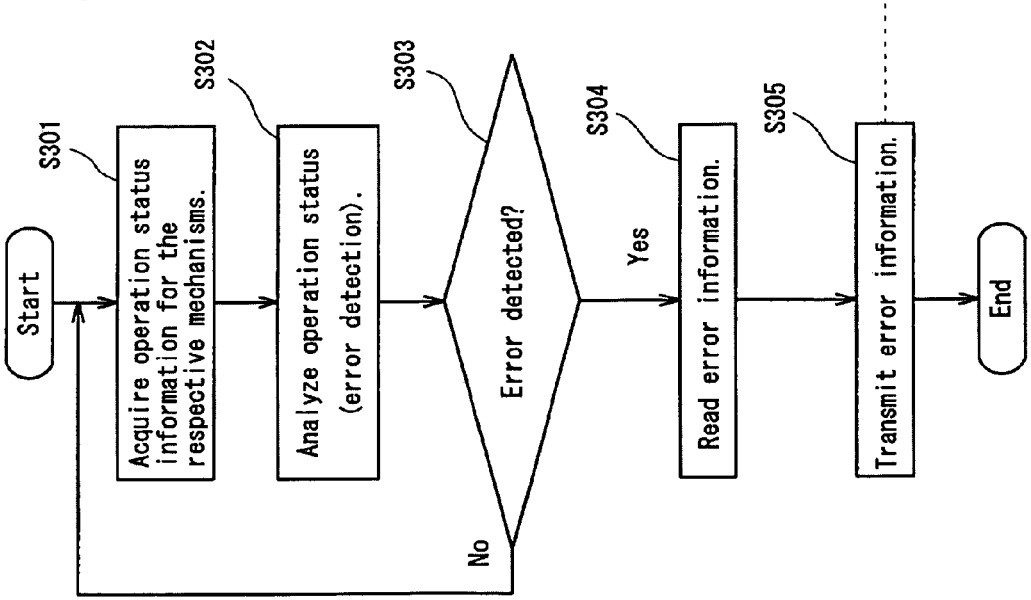

FIG. 5 is a flowchart illustrating the operation status check processing of the immunity analyzer 1. The respective mechanisms (components) constituting the measurement unit 2 such as the sample conveyor 10, the sample dispensing arm 50, and the reagent dispensing arms 90a to 90c include sensors 10s, 20s, 30s, 40s, 50s, 60s, 80sa, 80sb, 90s, 100s and 120s (sensing means) for monitoring the operation situations of the respective mechanisms (See FIG. 2). In Step S301, the main body controller 140 acquires the detection results from the respective sensors. In Step S302, the main body controller 140 analyzes the detection results (operation status information) acquired from the respective sensors. When an error occurs, the error is detected by this processing for analyzing the operation status. Next, Step S303 allows the main body controller 140 to determine whether the error is detected or not. When the main body controller 140 determines that the error is not detected, the processing returns to Step S301. When the main body controller 140 in Step S303 determines that the error is detected, error information is read in Step S304. This error information is information identifying the error (error ID). Then, the main body controller 140 in Step S305 sends the error information to the controller 400a, thereby completing the processing.

On the other hand, Step S401 allows the controller 400a to determine whether the error information is received or not. When the error information is received, the processing proceeds to Step S406 and an error processing (which will be described later) is executed. When the error information is not received on the other hand, the controller 400a in Step S402 acquires the operation status information of the control apparatus 400. This operation status information includes software internal status information and status information for hardware such as a communication interface. Then, the controller 400a in Step S403 analyzes the acquired operation status information. When an error occurs, the error is detected by this processing for analyzing the operation status. Next, Step S404 allows the controller 400a to determine whether the error is detected or not. When the error is not detected, the processing returns to Step S401. When the controller 400a in Step S404 determines that the error is detected, the error information is read in Step S405. Then, the controller 400a executes an error processing (which will be described next) (Step S406), thereby completing the processing.

Figure 7:
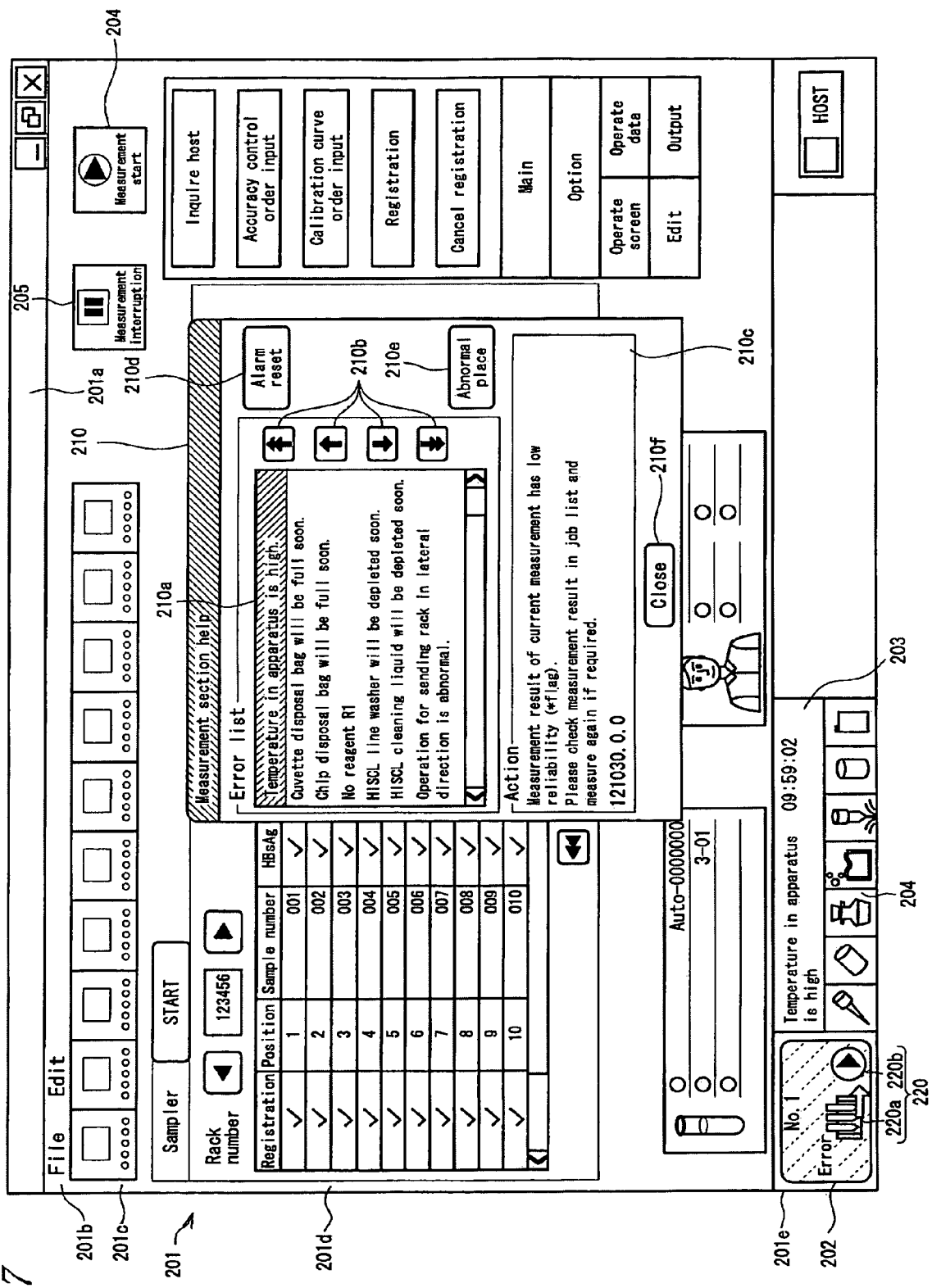
FIG. 7 illustrates a main window and a measurement section help window.

As shown in FIG. 7, this error processing is performed by providing a predetermined display on the apparatus status display area 202 of the main window 201 displayed on the display section 400b and by newly displaying a measurement section help window (error window) 210 on the display section 400b.

It is noted that the main window 201 is a window displayed in the display section 400b when an application program for controlling the measurement unit 2 is activated. The main window 201 has a title bar 201a, a menu bar 201b, a tool bar 201c, a main display block 201d, and an auxiliary display block 201e. In the example shown in FIG. 7, an order registration screen is displayed in the main display block 201c. The auxiliary display block 201d includes an apparatus status display area 202, a message display area 203, and a consumable supply information display area 204. The measurement section help window 210 is displayed in the main display block 201c of the main window 201 so as to be superposed on the previously-displayed screen.

The hard disk 401d of the controller 400a memorizes information regarding forms of various errors that may occur in the apparatus. Specifically, the hard disk 401d of the controller 400a memorizes pieces of information such as error titles (brief description of the errors), error-occurring places, and methods for recovering the errors so that the pieces of information are associated to one another. The information for the error-occurring place includes information for an image representing the place in a three-dimensional or two-dimensional manner (diagram, photograph, picture).

Figure 6:
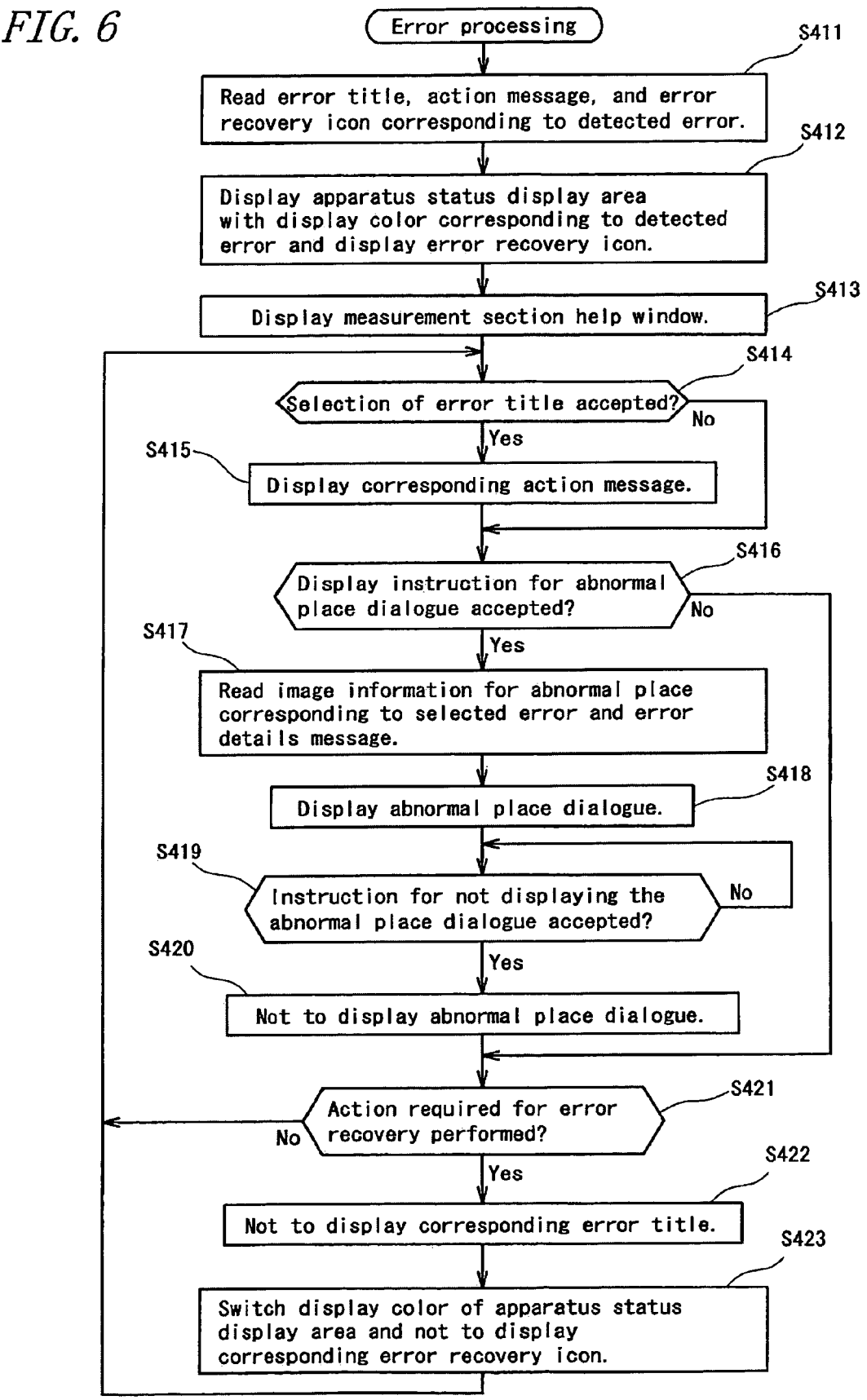
FIG. 6 is a flowchart illustrating the procedure of the error processing by the control apparatus.

FIG. 6 is a flowchart illustrating the error processing by the controller 400a. In Step S411 of FIG. 6, the controller 400a performs a processing for reading, from the hard disk 401d, an error title, an action message, and an error recovery icon corresponding to the detected error. The action message is mainly information regarding the method for recovering the error, and represents a procedure for recovering the error by a text. The error recovery icon 220 is similarly information regarding the method for recovering the error. As shown in FIG. 7, the error recovery icon 220 simply shows an operation that should be performed by a user in order to recover the error.

In Step S412 of FIG. 6, the controller 400a displays the apparatus status display area 202 by the display color corresponding to the detected error (which is shown by a dotted line hatching in FIG. 7 and the details of the display color will be described later). When there is the error recovery icon 220 corresponding to the error, the error recovery icon 220 is displayed in the apparatus status display area 202. Then, the measurement section help window 210 as shown in FIG. 7 is displayed on the main window 201 (Step S413). Alarm sound is also generated together with the display of the measurement section help window 210.

At the upper side of this measurement section help window 210, an error list (error title display area) 210a is provided. This error list 210a displays one or a plurality of detected error title(s). In the example shown in FIG. 7, the error list 210a displays seven error titles listed in the up-and-down direction. This error list 210a displays error titles in an order of priority. At the right side of the error list 210a, a button 210b for scrolling the error titles is provided. At the lower side of the measurement section help window 210, an action display area (recovery operation display area) 210c is provided. This action display area 210c displays an action message corresponding to the error title selected in the error list 210a.

In the initial status immediately after the activation of the measurement section help window 210, an error title at the top of the error list 210a is selected and an action message corresponding to the error title is displayed in the action display area 210c. When a user selects another error title, an action message corresponding to the error title is displayed in the action display area 210c.

In order to perform the processing as described above, the controller 400a in Step S414 of FIG. 6 determines whether the selection of another error title in the error list 210a is accepted or not. When the controller 400a determines that the selection of another error title in the error list 210a is accepted (Yes), the processing proceeds to Step S415. When the controller 400a determines that the selection of another error title in the error list 210a is not accepted (No), the processing proceeds to Step S416. The controller 400a in Step S415 displays an action message corresponding to the newly-selected error title in the action display area 210c.

The user can read the error title and the action message displayed in the measurement section help window 210 to perform an operation based on the procedure displayed in the action message, thereby recovering the error. The user also can select an alarm reset button 210d to stop the alarm sound.

As shown in FIG. 7, the apparatus status display area 202 displays the word "error" and also displays two error recovery icons 220a and 220b. The error recovery icon 220a is a "rack reset icon" instructing the reset of the rack 4. The error recovery icon 220b is a "measurement start icon" instructing the selection of the measurement start button 204 displayed at the upper-right part of the main window 201.

When the rack reset icon 220a and the measurement start icon 220b as described above are displayed in the apparatus status display area 202, the user can reset the rack 4 to the sample conveyor 10 and can select (or click) the measurement start button 204 of the main window 201 to resume the measurement. Specifically, the user can perform an operation based on the error recovery icon 220 displayed as an image in the apparatus status display area 202 to recover from the error status.

The image of the error recovery icon 220 is designed so as to allow the user to recognize how to operate. For example, the rack reset icon 220a is composed of a simple image schematically showing the rack 4 and an arrow showing the reset of the rack 4. The user can see the design of this image to associate the image with an operation that should be performed. The measurement start icon 220b has the same design as that of the measurement start button 204. Thus, the user can search and select a button having the same image as that of the measurement start icon 220b and thus is prevented from performing a wrong operation such as a case where the user mistakenly selects a wrong button.

The controller 400a can perform an operation for an error processing by displaying an abnormal place dialogue 230 (see FIG. 8) in addition to the measurement section help window 210. As shown in FIG. 7, this abnormal place dialogue 230 is a window that is newly activated when the "abnormal place" button 210e in the measurement section help window 210 is selected (or clicked). The abnormal place dialogue 230 can be optionally displayed when the user cannot recognize the error place only based on the contents displayed in the measurement section help window 210 or when the user wants to know detailed information for the error.

Figure 8:
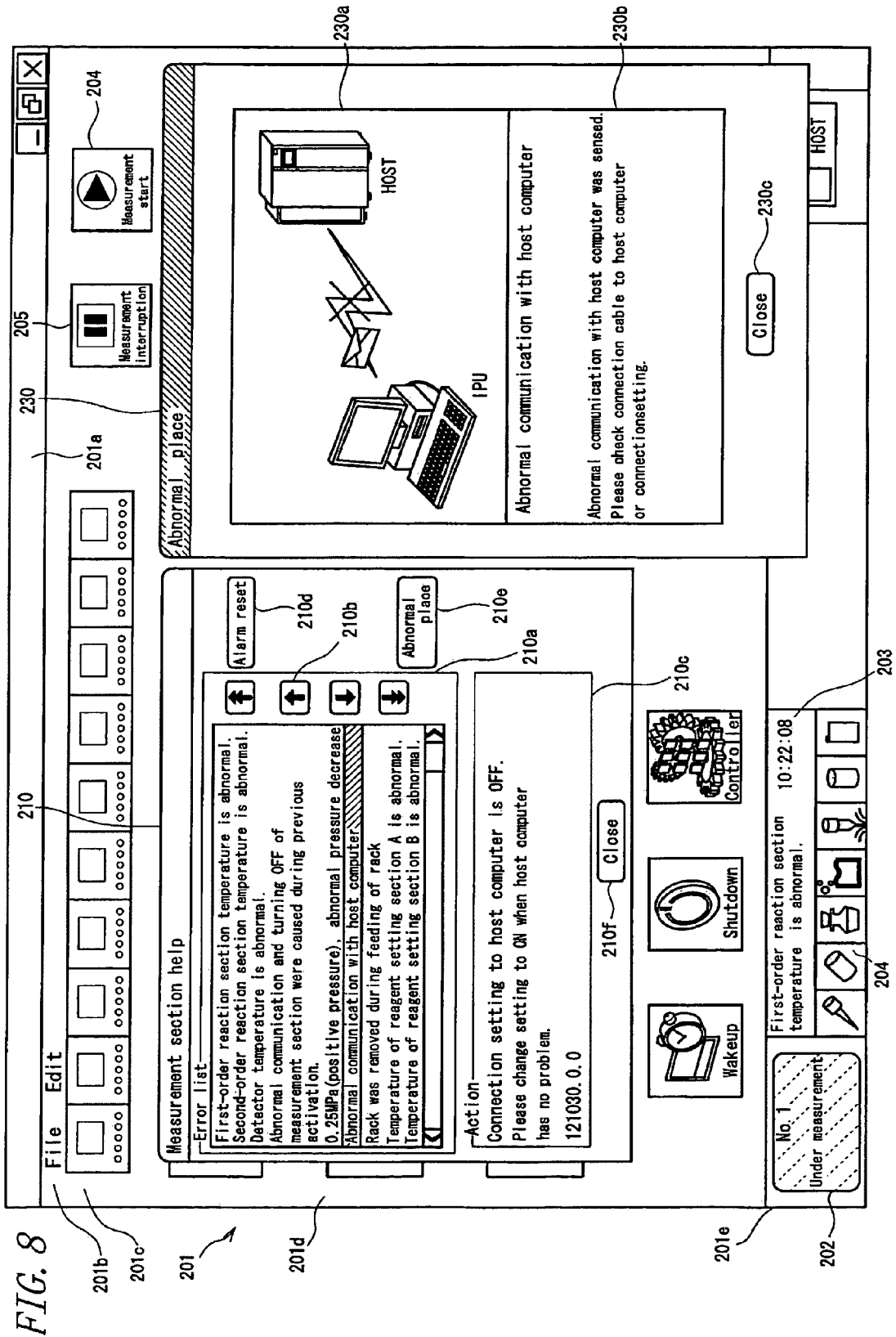
FIG. 8 illustrates the main window, the measurement section help window, and an abnormal place dialogue.

FIG. 8 shows the measurement section help window 210 having different contents from those shown in FIG. 7 and an abnormal place dialogue 230 corresponding to this measurement section help window 210. In the example shown in FIG. 8, an error title of "abnormal communication with host computer" is selected in the error list of the measurement section help window 210 and the corresponding action message of recovery information is displayed in the action display area 210c saying "Connection setting to host computer is OFF. Please change the setting to ON when the host computer has no problem".

When the user selects the abnormal place button 210e of this measurement section help window 210a, the abnormal place dialogue 230 as shown at the right side is activated. At the upper side of this abnormal place dialogue 230, the error place display area 230a displaying the error-occurring place by an image is provided. The error place display area 230a displays, by a three-dimensional image, a relation between the control apparatus 400 (IPU) and a host computer (HOST) connected to this control apparatus 400 so as to establish communication therebetween. At the lower side of the abnormal place dialogue 230, a detailed contents display area 230b is provided to display the detailed contents for an error (e.g., a cause of the error). Through the displayed abnormal place image as described above, the user can visually recognize that the error is caused in the control apparatus 400.

In order to perform the display of the abnormal place dialogue 230 as described above, the controller 400a in Step S416 of FIG. 6 determines whether the user has selected the abnormal place button 210e of the measurement section help window 210 or not (i.e., whether an instruction for displaying the abnormal place dialogue 210e is accepted or not). When the controller 400a determines that the instruction for displaying the abnormal place dialogue 230 is accepted (Yes), the controller 400a allows the processing to proceed to Step S417. When the controller 400a determines that the instruction for displaying the abnormal place dialogue 230 is not accepted (No), the processing proceeds to Step S421.

Step S417 allows the controller 400a to read, from the hard disk 401d, the abnormal place image and the error details message corresponding to the error title selected in the error list 210a. Step S418 allows the controller 400a to display the abnormal place dialogue 230.

Through the abnormal place image displayed in the error place display area 230a of the abnormal place dialogue 230, the user can visually recognize a place at which the error occurs. Specifically, when a user having a small operation experience cannot sufficiently understand the error-occurring place only based on the action message of the measurement section help window 210, the abnormal place dialogue 230 can be displayed to allow the user to accurately recognize the error-occurring place to recover the error. The user also can read the error details message displayed in the detailed contents display area 230b to obtain more detailed information for the error.

It is noted that, when the user can recover the error only based on the contents displayed in the measurement section help window 210, the user does not always have to display the abnormal place dialogue 230.

Figure 9:
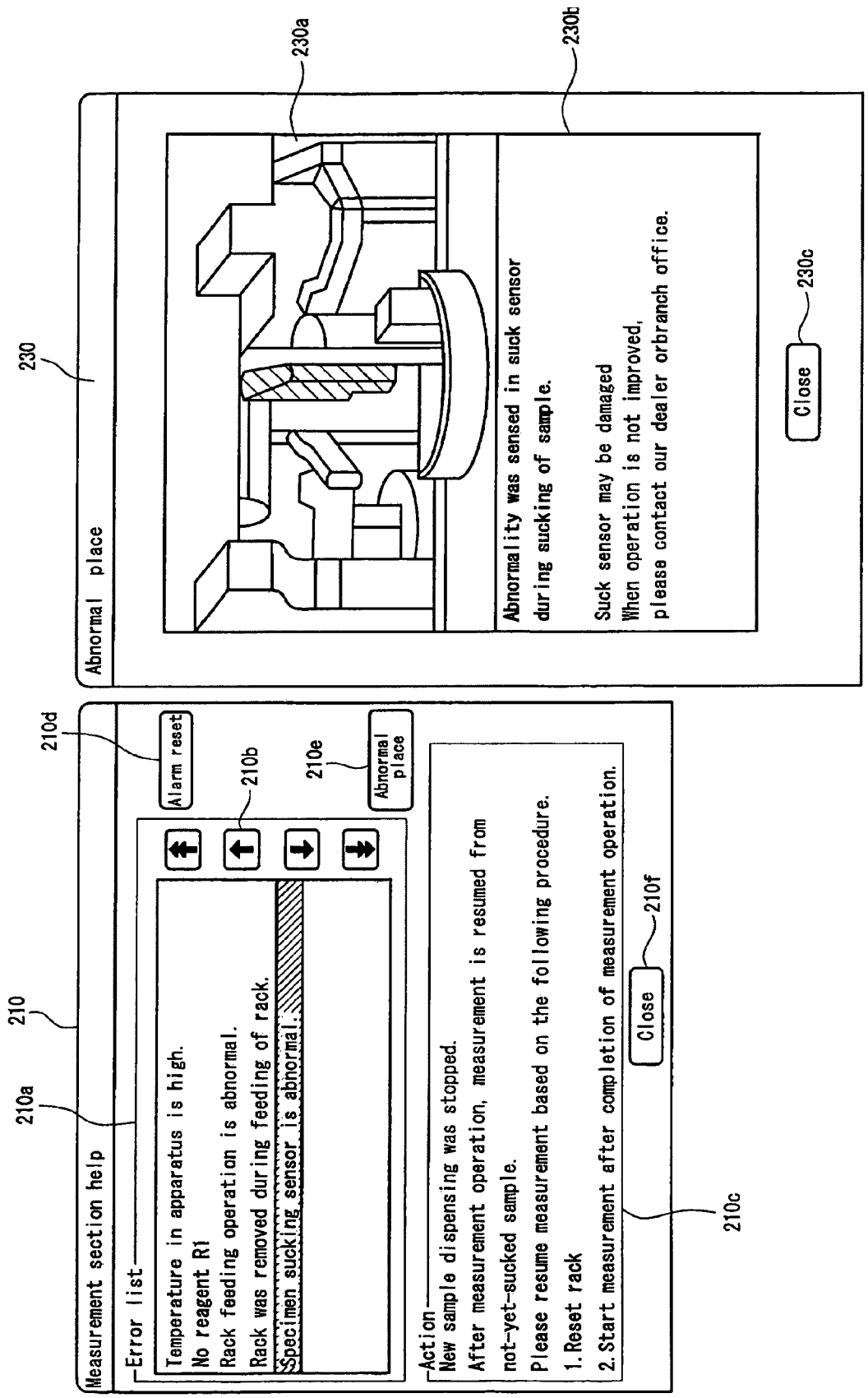
FIG. 9 illustrates another example of the measurement section help window and the abnormal place dialogue.

FIG. 9 shows the measurement section help window 210 according to another example and the abnormal place dialogue 230 corresponding to this measurement section help window 210. In the example shown in FIG. 9, an error title of "sample sucking sensor is abnormal" is selected in the error list 210a of the measurement section help window 210, and as the corresponding action message there is displayed, by text, the operation details for the measurement unit 2 regarding the error and a procedure for recovering the error. When the user selects the abnormal place button 210e, the abnormal place dialogue 230 is displayed. The error place display area 230a displays a three-dimensional image having the sample sucking portion (sample dispensing arm 50) at the center. The detailed contents display area 230b displays the cause of the error and how to do if the error is not recovered for example. The error place display area 230a displays the error place with a remarkable color (e.g., red, which is shown by hatching).

Figure 10:
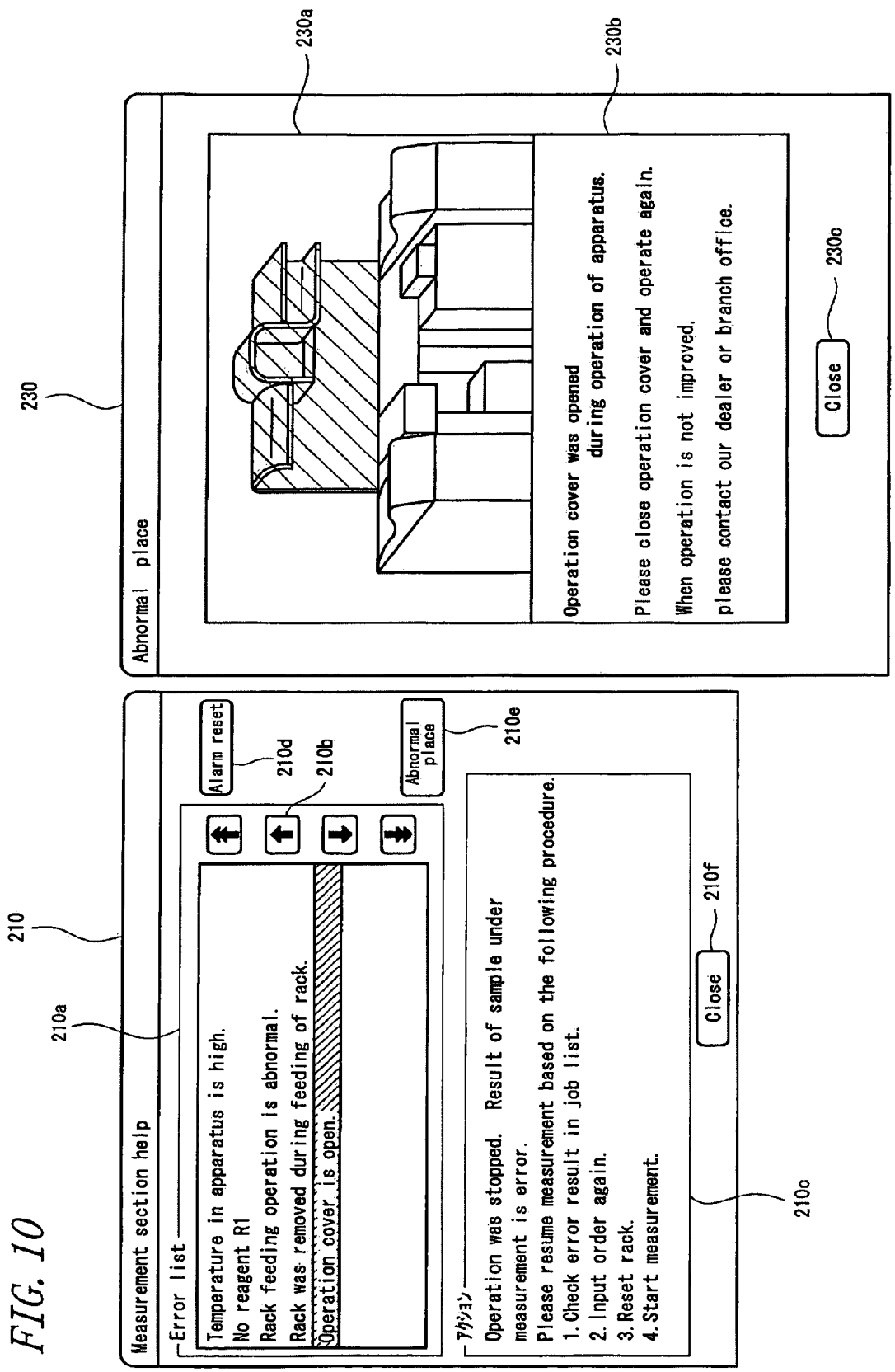
FIG. 10 illustrates a still another example of the measurement section help window and the abnormal place dialogue.

FIG. 10 shows the measurement section help window 210 according to a still another example and the abnormal place dialogue 230 corresponding to this the measurement section help window 210. In the example shown in FIG. 10, an error title of "operation cover is open." is selected in the error list 210a of the measurement section help window 210, and as the corresponding action message there is displayed, by text, the operation details for the measurement unit 2 regarding the error and a procedure for recovering the error. When the user selects the abnormal place button 210e, the abnormal place dialogue 230 is displayed. The error place display area 230a displays a three-dimensional image having the operation cover of the measurement section unit 2 at the center. The detailed contents display area 230b displays the cause of the error and how to do if the error is not recovered for example. The error place display area 230a displays the error place with a remarkable color (which is shown by hatching).

When the user wants to close the abnormal place dialogue 230 after recovering the error, the user selects a "close" button 230c of the dialogue 230. Then, the controller 400a in Step S419 of FIG. 6 determines whether the user has selected the "close" button 230c of the abnormal place dialogue or not (i.e., whether an instruction for not displaying the abnormal place dialogue 230 is accepted or not). When the instruction for not displaying the abnormal place dialogue 230 is accepted (Yes), the controller 400a allows the processing to proceed to Step S420 to carry out a processing to prevent the abnormal place dialogue 230 from being displayed (or to close the abnormal place dialogue 230).

Next, the controller 400a in Step S421 determines whether an operation (processing) required for the error recovery is performed or not. When the controller 400a determines that the operation is performed (Yes), the processing proceeds to Step S422. When the controller 400a determines that the operation is not performed, the processing returns to Step S414. Step S422 allows the controller 400a to delete the title of the recovered error from the error list 210a of the measurement section help window 210. Step S423 allows the controller 400a to optionally switch the display color of the apparatus status display area 202 (see FIG. 7) and to prevent the corresponding error recovery icon 220 from being displayed and the processing returns to Step S414.

[Apparatus Status Display Area]

FIG. 11 is a table showing, with regard to the apparatus status display area 202 shown in FIG. 7, the text displays, the display colors, the error recovery icons, and the apparatus statuses that associated to one another. The apparatus status display area 202 of the main window 201 displays the character information (text) showing the apparatus status of the measurement unit 2. The color of the entire area 202 in accordance with the apparatus status is switched to gray, blue, green, yellow, or red. In this embodiment, in accordance with the respective apparatus statuses shown by No. 1 to No. 15 of FIG. 11, the text data shown in the apparatus status display area 202, the background images of the apparatus status display area 202 of the respective display colors, and the error recovery icons are set in advance and are memorized in the hard disk 401d of the controller 400a so as to be associated to one another.

The color of the apparatus status display area 202 is "gray" when the power source of the measurement unit 2 is in an OFF status and the measurement cannot be performed (No. 1). The color of the apparatus status display area 202 is "blue" when the power source of the measurement unit 2 is ON but the measurement cannot be performed immediately (due to a pause status, a sleep status or the like) (No. 2 and No. 3). The color of the apparatus status display area 202 is "green" when the measurement unit 2 does not perform a measurement operation but the measurement can be started soon (No. 4 to No. 6). The color of the apparatus status display area 202 is "yellow" when the measurement unit 2 is performing a measurement operation, an initial operation, a maintenance operation (No. 7 to No. 14). The color of the apparatus status display area 202 is "red" when a fatal error occurs during the measurement and thus measurement cannot be performed (No. 15). The background images of the apparatus image display area 202 of the respective display colors associated with the respective apparatus statuses are memorized in the hard disk 401d.

In this embodiment, when some error occurs during the operation of the measurement unit 2 (when the display color is "yellow"), the above-described error recovery icon 220 (see FIG. 7) is displayed in the apparatus status display area 202. When an interruption button 205 (see FIG. 7) is depressed during the operation of the measurement unit 2 for example, the sucking of a new sample is stopped while an already-sucked sample being measured. In this case, as shown by No. 11 of FIG. 11, the yellow background image is displayed in the apparatus status display area 202 and the text of "being interrupted" is displayed and a "measurement start icon" 220b is displayed as the error recovery icon 220. When the error occurs, the user can select the measurement start button 204 (see FIG. 7) in accordance with the measurement start icon 220b to resume the measurement.

In this embodiment, as shown by No. 12 to No. 14 of FIG. 11, there are three patterns where the text of "error" is displayed during the operation of the measurement unit 2 (when the display color is "yellow"). In any of these error patterns, an already-sucked sample is still measured but the sucking of a new sample is stopped. No. 12 represents an error for which the measurement can be resumed by selecting the measurement start button 204. No. 13 represents an error for which the measurement can be resumed by resetting the rack 4 and selecting the measurement start button 204. No. 14 represents an error for which the measurement cannot be resumed until the rack 4 is reset to subsequently complete the current measurement (or an error for which the selection of the measurement start button 204 is not accepted).

In the case of No. 12, the measurement can be resumed only by selecting the measurement start button 204 and thus only the "measurement start icon" 220b is displayed in the apparatus status display area 202. In the case of No. 13, the measurement can be resumed by resetting the rack to subsequently select the measurement start button 204 and thus both of the "rack reset icon" 220a and the "measurement start icon" 220b are displayed. In the case of No. 14, the rack 4 must be reset but the measurement start button 204 cannot be selected. Thus, the "rack reset icon" 220a and the "measurement start impossible icon" (which is represented by adding symbol ⌊x⌋ to the measurement start icon) are displayed.

As described above, the color depending on the apparatus status of the measurement unit 2 is given to the apparatus status display area 202. Thus, the user can recognize, at a glance, whether the measurement unit 2 can be operated or not, or whether the measurement unit 2 already operates or not, for example.

The present invention is not limited to the above embodiment and also can be appropriately applied to different designs. For example, the abnormal place dialogue 230 and the measurement section help window 210 can be simultaneously displayed in the display section 400a or also may be integrated to one window. The present invention is not limited to the immunity analyzer and also can be used for other analysis apparatuses such as a blood coagulation analyzer, a multiple blood cell analysis apparatus, a formed urine component analysis apparatus, and a gene amplification measurement apparatus.

What is claimed is:

1. A sample analyzer for analyzing a sample, comprising:
   a detector for detecting an error that has occurred in the sample analyzer;
   an input device;
   a display; and
   a display controller for controlling the display so as to display a predetermined screen and a first window superposed on the predetermined screen;
   wherein the first window comprises:
      a first area for displaying an error list showing a plurality of errors detected by the detector;
      a second area for displaying recovery information for recovering from an error selected by the input device in the error list; and
      a button for displaying a second window displaying an image regarding a place where the selected error has occurred; and
   wherein the second window is displayed so as to be superposed on the predetermined screen without being superposed on the first window by the display controller when the button has been operated by the input device.

2. The sample analyzer of claim 1, further comprising:
   a memory for storing a plurality of recovery information and a plurality of images, wherein each of the images regards a place where an error has occurred;
   wherein the display controller reads out from the memory the recovery information for recovering from the selected error and the image regarding the place where the selected error has occurred, and controls the display so as to display the recovery information and the image read out from the memory.

3. The sample analyzer of claim 1, further comprising:
   a measurement section for measuring the sample;
      wherein the image displayed on the display shows a place in the measurement section where the error has occurred.

4. The sample analyzer of claim 3,
   wherein the image comprises an outside drawing of the measurement section comprising a unit where the error has occurred; and
   wherein the unit is so displayed as to be distinguishable from other units of the measurement section.

5. The sample analyzer of claim 1, wherein:
   the plurality of errors in the error list is displayed so as to be arranged in an order of priority, and recovery information for recovering from an error at a top of the error list is displayed in the second area when none of the plurality of errors in the error list has been selected by the input device.

6. The sample analyzer of claim 1, wherein a display color according to a status of the sample analyzer is displayed in the predetermined screen by the display controller.

7. The sample analyzer of claim 1, wherein a schematic image showing a recovery procedure for recovering from an error detected by the detector is displayed in the predetermined screen by the display controller.

8. A method for displaying error information of a sample analyzer for analyzing a sample, the method comprising:
   (a) displaying a predetermined screen on a display;
   (b) detecting a plurality of errors that have occurred in the sample analyzer;
   (c) displaying a first window comprising a first area and a second area so as to be superposed on the predetermined screen, the first area displaying an error list showing the plurality of errors detected in (b);
   (d) receiving a selection of an error in the error list;
   (e) displaying in the second area recovery information for recovering from the error selected in (d); and
   (f) displaying a second window displaying an image regarding a place where the selected error has occurred so as to be superposed on the predetermined screen without being superposed on the first window.

9. The method of claim 8,
   wherein the sample analyzer comprises a measurement section for measuring the sample; and wherein the image displayed in the second window shows a place in the measurement section where the error has occurred.

10. The method of claim 9,
wherein the image displayed in the second window comprises an outside drawing of the measurement section comprising a unit where the error has occurred; and
wherein the unit is so displayed as to be distinguishable from other units of the measurement section.

11. The method of claim 8, wherein:
(c) comprises displaying the plurality of errors in the error list so as to be arranged in an order of priority; and
wherein the method further comprises:
(g) displaying recovery information for recovering from an error at a top of the error list in the second area when none of the plurality of errors in the error list has been selected in (d).

12. The method of claim 8, further comprising:
(h) displaying a display color according to a status of the sample analyzer in the predetermined screen.

13. The method of claim 8, further comprising:
(i) displaying in the predetermined screen a schematic image showing a recovery procedure for recovering from an error.

* * * * *